US007292718B2

(12) United States Patent
Douglass

(10) Patent No.: US 7,292,718 B2
(45) Date of Patent: Nov. 6, 2007

(54) COLOR SPACE TRANSFORMATIONS FOR USE IN IDENTIFYING OBJECTS OF INTEREST IN BIOLOGICAL SPECIMENS

(75) Inventor: James Douglass, Indialantic, FL (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 11/528,080

(22) Filed: Sep. 26, 2006

(65) Prior Publication Data

US 2007/0041627 A1 Feb. 22, 2007

Related U.S. Application Data

(62) Division of application No. 10/282,362, filed on Oct. 28, 2002, now Pat. No. 7,200,252.

(51) Int. Cl.
*G06K 9/00* (2006.01)
(52) U.S. Cl. ............... 382/128; 382/133; 382/162; 382/164; 382/276
(58) Field of Classification Search ........... 382/128, 382/130, 132–133, 162, 164, 224–225, 276
See application file for complete search history.

(56) References Cited

U.S. PATENT DOCUMENTS

| 3,824,393 | A | 7/1974 | Brain ..................... 250/222.1 |
| 5,016,173 | A | 5/1991 | Kenet et al. ............ 364/413.13 |
| 5,202,931 | A | 4/1993 | Bacus ..................... 382/133 |
| 5,231,580 | A | 7/1993 | Cheung et al. .......... 364/413.13 |
| 5,257,182 | A | 10/1993 | Luck et al. ............. 364/413.1 |
| 5,268,966 | A | 12/1993 | Kasdan .................... 382/133 |
| 5,287,272 | A | 2/1994 | Rutenberg et al. ...... 364/413.01 |
| 5,333,207 | A | 7/1994 | Rutenberg .................. 382/6 |
| 5,375,177 | A | 12/1994 | Vaidyanathan et al. ...... 382/48 |

(Continued)

FOREIGN PATENT DOCUMENTS

EP     0798550     10/1997

(Continued)

OTHER PUBLICATIONS

Baxes, G.A., "Digital Image Processing," John Wiley & Sons, Inc., *Image Analysis*, pp. 127-137.

(Continued)

*Primary Examiner*—Bhavesh M Mehta
*Assistant Examiner*—John B Strege
(74) *Attorney, Agent, or Firm*—McDonnell Boehnen Hulbert & Berghoff LLP

(57) ABSTRACT

Two color transformations, as described herein, facilitate identification of the objects of interest in the biological specimen. One of the color transformations, a Minus Clear Plus One (MC+1) transformation, can be conceptualized as either translating and rotating axes of a three-dimensional coordinate space that defines an image of the biological specimen or calculating differences between vectors in the three dimensional coordinate space that defines the image of the biological specimen. The other of the color transformations, a Quantitative Chromatic Transformation (QCT), is a calorimetric transformation that produces three new quantities from the original red, green, and blue pixel values for each color pixel of an image. These three new quantities, X, Y, and Z can each be related to the quantitative amount of absorbing molecules sampled by that pixel. Application of one or both of the color transformations to the image of the biological specimen results in a transformed image, in which objects of interest are more readily identifiable.

12 Claims, 7 Drawing Sheets

U.S. PATENT DOCUMENTS

| | | | |
|---|---|---|---|
| 5,428,690 A | 6/1995 | Bacus et al. | 382/128 |
| 5,449,622 A | 9/1995 | Yabe et al. | 436/63 |
| 5,499,097 A | 3/1996 | Ortyn et al. | 356/372 |
| 5,585,469 A | 12/1996 | Kojima et al. | 534/573 |
| 5,625,705 A | 4/1997 | Recht | 382/128 |
| 5,740,270 A | 4/1998 | Rutenberg et al. | 382/133 |
| 6,151,405 A | 11/2000 | Douglass et al. | 382/133 |
| 6,215,892 B1 | 4/2001 | Douglass et al. | 382/128 |
| 6,330,349 B1 | 12/2001 | Hays et al. | 382/128 |
| 6,553,135 B1 | 4/2003 | Douglass et al. | 328/128 |
| 6,577,754 B2 | 6/2003 | Stone et al. | 382/133 |
| 2003/0091221 A1 | 5/2003 | Marcelpoil et al. | |
| 2003/0138140 A1 | 7/2003 | Marcelpoil et al. | |

FOREIGN PATENT DOCUMENTS

| | | |
|---|---|---|
| EP | 1120274 | 8/2001 |
| WO | WO 9844333 | 10/1998 |

OTHER PUBLICATIONS

Simpson, J.L. and Elias, S., "Isolating Fetal Cells from Maternal Blood—Advances in Prenatal Diagnosis Through Molecular Technology," *JAMA*, vol. 270, No. 19, pp. 2357-2361 (Nov. 17, 1993).

Price, J.O., et al. "Prenatal Diagnosis with Fetal Cells Isolated from Maternal Blood by Multiparameter Flow Cytometry," *AM. J. Obstet. Gynecol.*, vol. 165, pp. 1731-1737 (Dec. 1991).

Mansi, J.L., et al., "Bone Marrow Micrometastases in Primary Breast Cancer: Prognostic Significance after 6 Years' Follow-up," *Eur. J. Cancer*, vol. 27, No. 12, pp. 1552-1555 (1991).

Cote, R. J., et al., "Prediction of Early Relaspe in Patients with Operable Breast Cancer by Detection of Occult Bone Marrow Micrometastases," *Journal of Clinical Oncology*, vol. 9, No. 10, pp. 1749-17562 (Oct. 1991).

Moss, T.J., et al., "Prognostic Value of Immunocytologic Detection of Bone Marrow Metastases in Neuroblastoma," *The New England Journal of Medicine*, vol. 324, No. 4, pp. 219-226 (Jan. 24, 1991).

McAulay et al., "Adaptive Color Basis Transformation an Aid in Image Segmentation", The International Academy of Cytology, Analytical and Quantitative Cytology and Histology, vol. 11 No. 1, pp. 53-58 (Feb. 1998).

Umbaugh et al., "Automatic Color Segmentation of Images with Application to Detection of Variegated Coloring in skin Tumors", IEEE Engineering in Medicine and Biology Magazine, pp. 43-52 (Dec. 1989).

Partial European Search Report in EP 03 25 6825 dated Mar. 11, 2004.

COLOR SPACE TRANSFORMATIONS FOR USE IN IDENTIFYING OBJECTS OF INTEREST IN BIOLOGICAL SPECIMENS

CROSS-REFERENCE TO RELATED APPLICATION

This is a divisional of prior U.S. application Ser. No. 10/282,362, filed Oct. 28, 2002 now U.S. Pat. No. 7,200,252, the content of which is incorporated by reference herein.

BACKGROUND

1. Field of the Invention

This invention relates generally to the field of identification and analysis of biological specimens, and more particularly to a method and system for identifying objects of interest, such as cancerous cells or cellular objects, in a biological specimen. The invention is also related to the field of color space transformations, in which a representation of an object in one color space (e.g., red, green and blue components) is transformed mathematically into a new representation in a new color space, in order to more easily observe or identify objects.

2. Description of Related Art

A biological specimen such as samples of bone marrow, cervical tissue, lymph nodes, or peripheral blood, may have objects of interest to a pathologist or histologist. Such samples are typically fixed to a slide and examined under a microscope. An important aspect of medical diagnostics is detecting, identifying, and quantitating the objects of interest within the biological specimen. The objects of interest may be, for example, cancer cells, cell objects such as nuclei, or particular proteins or clusters of proteins present in the biological specimen. The cancer cells or the particular proteins in the biological specimen can be difficult to detect. However, by staining the biological specimen with a stain, the objects of interest in the biological specimen can be made more readily identifiable.

A staining process involves introducing a probe that is reactive with a component of the objects of interest. The probe typically is a monoclonal antibody, a polyclonal antiserum, or a nucleic acid that reacts with the component of the objects of interest. Another probe with an enzyme, such as alkaline phosphatase or glucose oxidase then detects a reaction. The probe with the enzyme produces an enzymatic reaction that results in the objects of interest being stained a particular color. On the other hand, background areas and normal cells, for example, are stained colors, different from the particular color. Thus, the enzymatic reaction makes identifiable the objects of interest, if any, from the background areas and normal cells of the biological specimen.

A lab technician can manually examine the biological specimen to identify the objects of interest with a microscope. Recently, however, automated microscope systems and associated software for image analysis of the captured images of the slides have been developed to examine the biological specimen. These systems improve speed and accuracy in identifying the objects of interest in the biological specimen.

For example, U.S. Pat. No. 6,215,892 ('892 patent), assigned to ChromaVision Medical Systems, discloses an apparatus for automated cell analysis. The apparatus consists of a microscope with objective lenses, a stage for holding a slide, and a charged coupled device (CCD) camera. The slide includes the biological specimen to be examined. As a result, the CCD camera can capture an image of the biological specimen at a magnification level determined by the objective lenses.

The image of the biological specimen facilitates identification of the objects of interest. Picture elements, i.e., pixels, typically define the image of the biological specimen captured by the camera. Each of the pixels is made up of three components: a red component, a green component, and a blue components. Separate red, blue and green CCD cameras can be used to generate the red, blue and green pixels. The image of the biological specimen, i.e., the pixels defined by the red components, green components, and blue components, are transformed into a new representation or form. The new representation or form makes the objects of interest within the biological specimen readily identifiable.

The process of mathematically transforming an image from one representation, into another representation or form is known as applying a "color space transformation." Several such color transformations exist, including hue saturation and intensity transformations, and a color transformation described in the '892 patent. The color space transformation described in the '892 patent involves forming a ratio of two different color components for each pixel in the image of the biological specimen. The ratio provides a means for discriminating color information. With three components for each pixel, nine possible color ratios can be formed: R/R, R/G, R/B, G/G, G/B, G/R, B/B, B/G, and B/R. The ratio to select for the color transformation depends on a range of colors expected in the biological specimen. For example, typical stains used for detecting objects of interest such as tumor cells are predominately red, as opposed to predominately green or blue. Thus, the pixels of an object of interest contain a red component which is larger than either the green or blue components. A ratio of red divided by blue (R/B) provides a value which is greater than one for tumor cells, but is approximately one for any clear or white areas on the slide. Since the remaining cells, i.e., normal cells, typically are stained blue, the R/B ratio for pixels of these latter cells yield values of less than one. The R/B ratio is preferred for clearly separating color information typical in these applications. Those pixels having color ratios that exceed a threshold level are associated with the objects of interest.

The automated cell analysis improves speed and accuracy in identifying the objects of interest in the biological specimen. The lab technician can manually review and evaluate whether pixels having ratios that exceed the threshold level are associated with the objects of interest. The lab technician need not manually analyze the biological specimen, as a whole, to identify the objects of interest.

It is not uncommon that areas of intense staining or foreign debris, such as dirt, appear on the slide. The areas of intense staining and foreign debris can cause the ratio-based color transformation of the '892 patent to improperly characterize the areas of intense staining or foreign debris as objects of interest. Since the components of the pixels in such areas are relatively "low," and since low components that make up such pixels can appear in the denominator of the ratios, the color ratio can have falsely high values, causing "false" objects of interest to appear. These false objects of interest are objects identified as being objects of interest, but are in fact either normal cells or background areas of the biological specimen.

A presence of false objects of interest associated with the ratio-based color transformation drives one to use extensive morphological processing following the color transformation to recognize and attempt to eliminate the false objects of interest. Therefore, there exists a need for a method and system to more reliably identify objects of interest in the biological specimen, which is less sensitive to intense staining or foreign debris produced as a result of the staining process.

SUMMARY

Methods are provided herein for identifying objects of interest, which take advantage of using one or more novel color space transformations described herein. Several methods are described herein for conceptualizing the color space transformations, and for carrying out the transformations in practice using a general-purpose computer. The methods described below are preferably coded in software as a set of instructions for the general-purpose computer. The methods are particularly designed for use in processing an image having red green and blue pixel components and transforming that image to another representation with the computer and displaying the transformed image to the user. The transformed image enables a human operator (e.g., pathologist or technician) to more readily observe and identify objects of interest that are contained in specimen.

The first transformation, referred to herein as "Minus Clear Plus One" or "MC+1", is suited to staining methods that produce at least two different colors. Conceptually, the MC+1 transformation involves translating and rotating axes of a three-dimensional coordinate space that defines an image of the biological specimen. Alternatively, the MC+1 transformation involves calculating differences between vectors in the three dimensional coordinate space. The MC+1 transformation has a high degree of sensitivity to objects of interest, while being insensitive to characterizing areas of intense staining or foreign debris produced as a result of the staining as objects of interest. Therefore, the MC+1 transformation does not produce false identification of objects of interest, typical of the ratio-based color transformation.

The other of the color space transformations is referred to herein as the "Quantitative Chromatic Transformation" or "the QCT". Like the MC+1 transformation, the QCT is also sensitive to identifying objects of interest, but insensitive to characterizing areas of intense staining or foreign debris produced as a result of the staining as objects of interest. The QCT quantitates, for each pixel, a number of absorbing molecules. The QCT produces quantities that are linearly related to concentration of analytes and is robust in the presence of instrument calibration errors. The QCT has a high specificity to colors of interest in the biological specimen and does not introduce quantitation errors, also typical of the ratio-based color transformation.

Application of one, or both, of the above two color transformations to the image of the biological specimen results in a transformed image (or transformed images if both are used) that aid in the identification of the objects of interest in the biological specimen.

According to one exemplary embodiment of the present invention, the MC+1 color transformation involves reorienting the three-dimensional coordinate space defining the image of the biological specimen. The three-dimensional coordinate space has axes corresponding to the red component, green component, and blue component of the pixels in the image of the biological specimen. In the three-dimensional coordinate space, positive object pixels define the objects of interest in the biological specimen, counter-stained object pixels define normal cells in the biological specimen, and background pixels define background areas, e.g., clear areas, of the biological specimen. The three-dimensional coordinate space is reoriented such that a cluster of the background pixels is at an origin of the three-dimensional coordinate space and the counter-stained object pixels lie substantially along an axis of the three-dimensional coordinate space. As a result, the positive object pixels, defining the objects of interest, if any, lie substantially between the axes of the three-dimensional coordinate space.

According to an alternative exemplary embodiment of the present invention, the MC+1 color transformation, described above as reorienting the three dimensional coordinate space, may be mathematically characterized by a sum of products for each of the pixels in the image of the biological specimen. Coefficients and complements define the sum of products. Stains which identify the objects of interest in the biological specimen define the coefficients for the MC+1 transformation. On the other hand, the complements are defined by the difference between the actual value of the red component and a maximum value of the red component, the actual value of the green component and the maximum value of the green component, and the actual value of the blue component and the maximum value of the blue component. The sum of the products between the coefficient and the complements, for each pixel, produces a transformed image which identifies the objects of interest, if any, in the biological specimen.

According to yet another alternative exemplary embodiment of the present invention, the MC+1 transformation may be implemented by calculating differences between vectors in the three-dimensional coordinate space. A counter-stained object vector extends from a cluster of the background pixels through counter-stained object pixels in the three-dimensional space. On the other hand, a positive object vector extends from the cluster of the background pixels to a positive object pixel also in the three dimensional space. The image of the biological specimen is transformed by calculating, for each pixel, a difference between the positive object vector and the counter-stained object vector. The differences for each of the pixels define a transformed image which identifies the objects of interest, if any, in the biological specimen.

According to an alternative exemplary embodiment of the present invention, the MC+1 transformation, described above as calculating differences between vectors, may be mathematically characterized by executing instructions in software that calculate a transform value, for each pixel, the value defined by a square root of $(p_1^2+p_2^2+p_3^2) \times (p_{1c}^2+p_{2c}^2+p_{3c}^2)-(p_1 \times p_{1c}+p_2 \times p_{2c}+p_3 \times p_{3c})^2$. Quantities $p_1$, $p_2$, and $p_3$, reprresent a complement of first component, e.g., red component, second component, e.g., green component, and third component, e.g., blue component, respectively, of a pixel to be transformed. On the other hand, quantities $p_{1c}$, $p_{2c}$, and $p_3$ represent a complement of the first component, a complement of the second component, and a complement of the third component, respectively of a representative counter-stained pixel. The transform values for each of the pixels define a transformed image which can be used by an operator or through software to identify the objects of interest, if any, in the biological specimen.

The Quantitative Chromatic Transform is a calorimetric transformation that produces three new quantities from the original red, green, and blue pixel values for each color pixel of an image. These three new quantities, X, Y, and Z can each be easily related to the quantitative amount of absorbing molecules sampled by that pixel by the logarithm function. The distinctive feature of the QCT, is its ability to quantitate analytes from color image data.

The QCT transformation can be implemented by calculating a quotient between a first value and a second value, the quotient defining the number of absorbing molecules, per pixel. The first value is a square of a first component, e.g., red, green, or blue component, of a pixel to be transformed. The second value, on the other hand, is a product of a second component, e.g., also red, green, or blue component of the pixel to be transformed, and a third component, e.g., red, green, or blue component of the pixel to be transformed. The number of absorbing molecules for each pixel defines a transformed image which identifies the objects of interest, if any, in the biological specimen.

These as well as other aspects and advantages will become apparent to those of ordinary skill in the art by reading the following detailed description, with appropriate reference to the accompanying drawings.

BRIEF DESCRIPTION OF THE DRAWINGS

Exemplary embodiments of the present invention are described herein with reference to the drawings, in which.

DETAILED DESCRIPTION OF PREFERRED EMBODIMENTS

Figure 1:
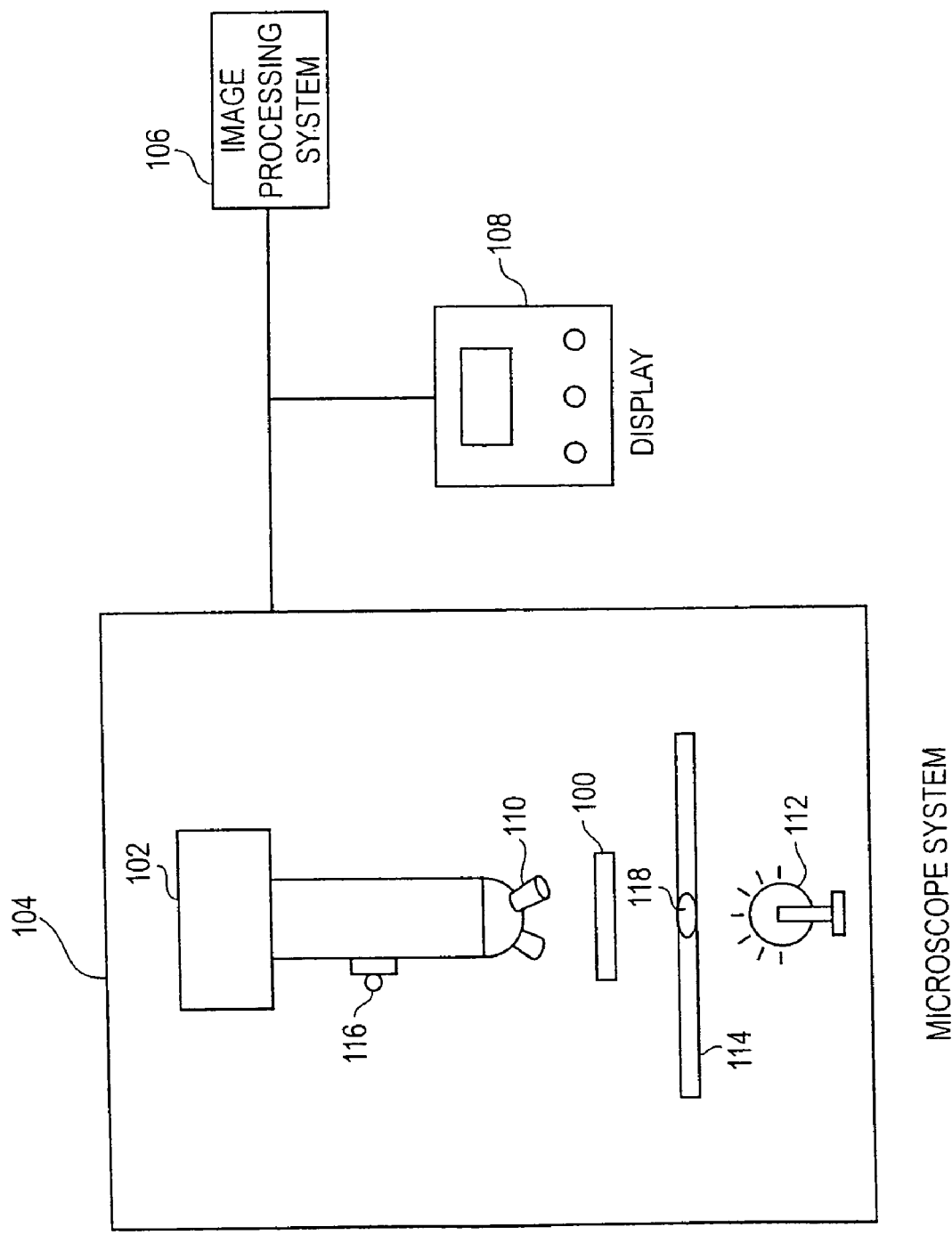
FIG. 1 is a block diagram of a representative apparatus for automated cell analysis of a biological specimen.

FIG. 1 is a block diagram of exemplary apparatus for automated cell analysis of a biological specimen, in which exemplary embodiments of the present invention may be employed. It should be understood that this and other arrangements and elements (e.g., machines, interfaces, functions, orders of elements, etc.) can be added or used instead and some elements may be omitted altogether. Additionally, those skilled in the art will appreciate that many of the elements described herein are functional entities that may be implemented as discrete components or in conjunction with other components, in any suitable combination and location.

Moreover, the various functions described herein as being performed by one or more entities may be carried out by hardware or by a processor programmed to execute an appropriate set of computer instructions stored in memory. Provided with the present disclosure, those skilled in the art can construct the hardware and develop the appropriate set of computer instructions to perform such functions. Indeed, the invention is suitable for use with existing microscope systems in current use today, including those supplied by Chromavision, Bacus Laboratories, Accumed International (now Molecular Diagnostics, Inc.) and others, with the associated computers of such systems being modified to include code performing the color space transformations described herein.

By way of example, the apparatus for performing the automated cell analysis may include a microscope system 104, an image processing system 106, and a display 108. The microscope system 104 allows for obtaining an image of the biological specimen contained on a slide 100 by means of an charged coupled device (CCD) camera 102 having appropriate red, blue and green filters, or separate red blue and green CCD cameras. The microscope system 104 has a motorized X-Y stage 114 holding the slide, a Z stage focus 116, objective lenses 110, a light source 112. The X-Y stage 114 allows for the slide 100 to be moved horizontally in an X-Y plane so that the biological specimen is under the objective lenses 110. X-Y positions where the slide is imaged in particular fields of view may be recorded and stored for future reference, or other means may be used to store locations on the slide where particular fields of view are obtained.

The objective lenses 110 magnify the biological specimen 100 so that individual cells, cellular structure, and other matter in the biological specimen can be discriminated. The microscope system also has the Z stage focus 116. The Z stage focus 116 adjusts displacement of the X-Y stage 114 in a Z direction. The displacement of the X-Y stage 114 in the Z direction allows for focusing the biological specimen while under the objective lenses 110.

The camera 102 captures an electronic image of the biological specimen so that objects of interest can be identified in the biological specimen. The light from the source 112 passes through the biological specimen mounted on the slide 100, and is imaged by the objective lenses 110 on the focal plane of the CCD camera. The camera 102 captures an in-focus, magnified, electronic image of the biological specimen for analysis that is converted to digital form and stored in memory.

A digital link, e.g., data bus or communication network, connects the image processing system 106 to the microscope system 104. The microscope system 104 sends the image of the biological specimen (i.e., the electronic image) to the image processing system 106 so that a color transformation, i.e., the MC+1 transform or QCT, as described herein, can be applied to the image. The image processing system 106 may take the form of a general purpose computer having a processor (CPU) and a main memory. The memory stores computer instructions executable by the processor for applying the MC+1 transform and/or the QCT to the image of the biological specimen. As a result of applying the color transformation, the image processing system 106 produces a transformed image in which the objects of interest in the biological specimen, if any, are identifiable.

Additionally, if so equipped, the image processing system 106 may send the transformed image to a display screen 108. The display screen 108 may be a monochrome or color display coupled to the image processing system 106. The display screen 108 may present the transformed image on the display screen 108 so that a lab technician, for example, can see whether the biological specimen has any objects of interest.

Figure 2:
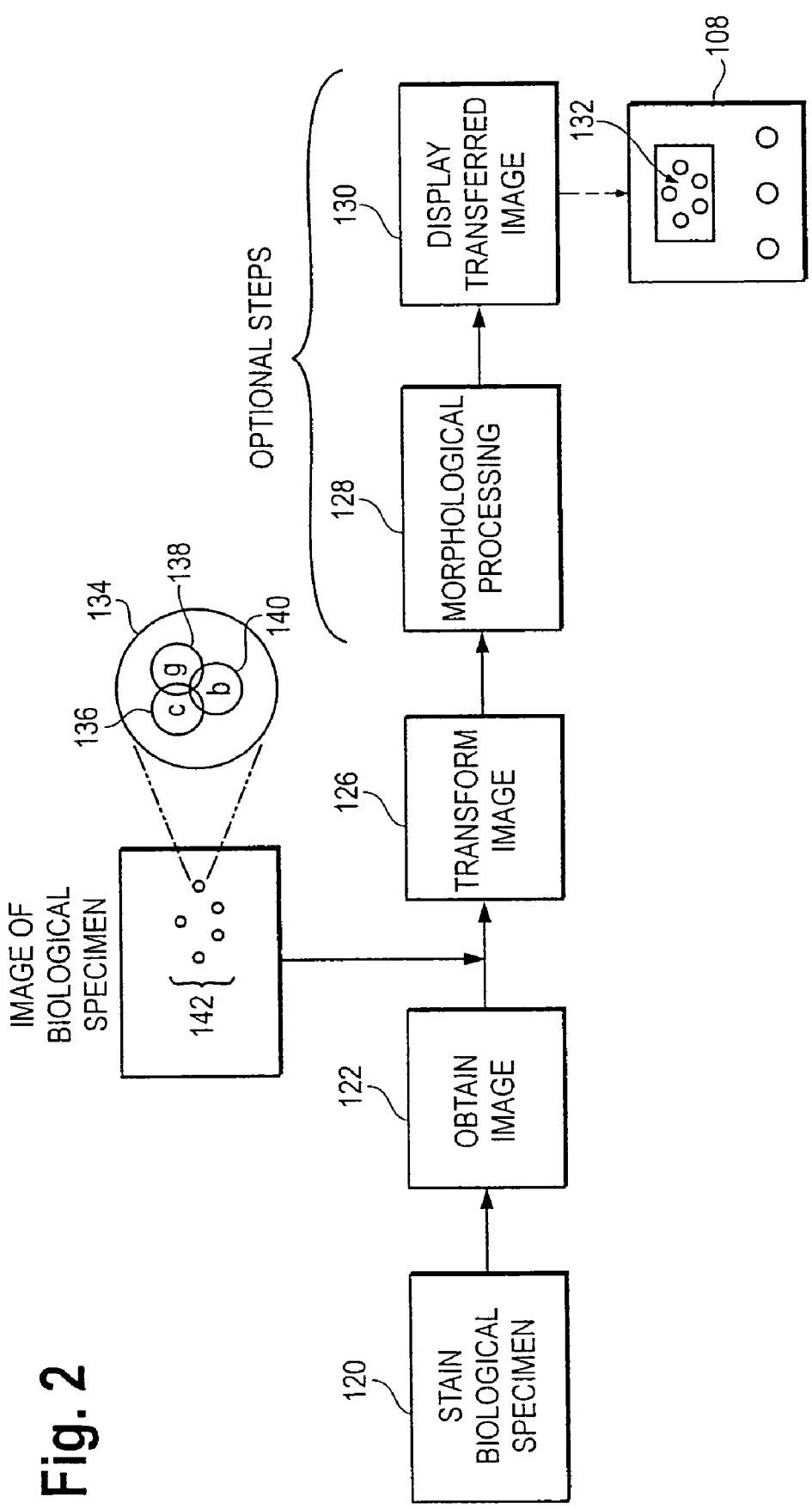
FIG. 2 illustrates a process for identifying objects of interest in the biological specimen.

FIG. 2 illustrates, in more detail, a process for identifying objects of interest in the biological specimen that employs exemplary apparatus of FIG. 1.

At step 120, the biological specimen is stained with one or more probes. The MC+1 transformation and the QCT performed by the image processing system 106 rely on the objects of interest being stained a different color from normal cells and background areas of the biological specimen. As a result, the biological specimen is stained with the one or more probes prior to obtaining the image of the stained biological specimen.

The one or more probes consist of reagents and/or enzymes that react differently with the cells, structures, and other matter defining the biological specimen 100. For example, the probes typically result in the objects of interest reacting with the probe to produce a stain with a first color, the normal cells reacting with the probe to produce a stain with a second color, and, if the biological specimen is mounted on a slide, background areas, i.e., clear areas, being unstained. Of course, other arrangements are also possible depending on the stains employed.

At step 122, the microscope system 104 obtains the image of the biological specimen. Pixels typically define the image of the biological specimen (i.e., the cells, structure, and other matter in the biological specimen). Each of the pixels 142 may consist of a cluster of colors 134, e.g., a red component 136, a green component 138, and a blue component 140. Alternatively, the image of the biological specimen may be defined by pixels with components such as luminance and chrominance components (Y, Cr, Cb) or hue, saturation, intensity (H, S, I) components. Preferably, however, the image may be defined by the pixels with the red components, the green components, and the blue components. These components are digitized in memory in a scale of 0 to 255 with higher numbers representing more intensity.

The pixels in the image may be classified as positive object pixels, i.e., associated with the objects of interest, and counterstained object pixels, i.e., associated with normal cells. Moreover, if the biological specimen in mounted on a slide, then clear areas of the slide may be classified as background area pixels. The staining by the one or more probes results in the positive object pixels taking on a different color from the normal pixels and the background area pixels of the biological specimen. For example, the objects of interest may take on a reddish brown color while normal cells may take on a grayish color. If the biological specimen is mounted on a clear slide, then the background areas may take on a whitish color. Of course, other arrangements are also possible depending on the particular staining method in use.

At step 126, the image processing system will transform the image of the biological specimen to produce a transformed image. A processor on the image processing system 106 executes the computer instructions stored in memory that define one of two color transformations, the MC+1 transformation and QCT. The color transformation allows for automated identification of the objects of interest in the biological specimen from normal cells and background areas. The color transformation produces a new set of pixel values, i.e., the transformed image, in which the normal cells and the background areas are identifiable from the objects of interest.

If so equipped, the automated cell analysis apparatus may perform steps 128 and 130. At step 128, the image processing system may, but need not, morphologically process the transformed image. Application of morphological processing further refines the identification of the objects of interest within the biological specimen. For example, the morphological processing results in boundaries of the cells of interest in the biological specimen being more clearly identified. The image processing system may use standard techniques, such as dilation or erosion, well known to those skilled in the art, to perform the morphological processing.

Additionally, if the image processing system 106 is coupled to a display, then, at step 130, the image processing system will present the transformed image 132 on the display. The image processing system 104 typically presents the transformed image on the display in a manner such that the objects of interest are presented at a different intensity or color from that of the normal cells and the background areas. By presenting the objects of interest at the different intensity, the transformed image identifies the objects of interest, if any, in the biological specimen.

As noted above, the image processing system 106 uses a color transformation to identify the objects of interest in the image of the biological specimen 124. The image processing system applies the MC+1 transformation, the QCT, or both transformations, to produce the transformed image identifying the objects of interest. Advantageously, the MC+1 transformation and QCT allows for identifying the objects of interest with a high degree of quantitation, without falsely identifying, as objects of interest, areas of intense staining or presence of foreign objects, produced as a result of the staining.

MC+1 Transformation

The MC+1 transformation is suited to identifying objects of interest in the image of the biological specimen, when the staining methods produce at least two different colors. The MC+1 transformation results a transformed image where the normal cells and the background areas are close to black and the objects of interest are close to white. Hence, the name minus clear (MC, e.g., minus or subtraction of normal cells and background areas), plus one (e.g., positive objects).

Figure 3:
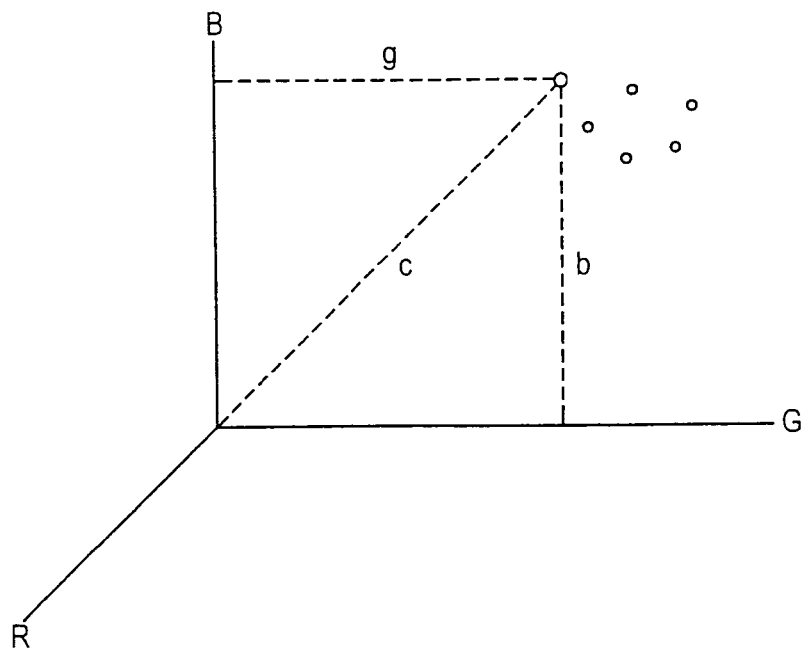
FIG. 3 illustrates a pixel plotted in a three-dimensional coordinate space.

Conceptually, the MC+1 transformation involves visualizing pixels in the image of the biological specimen as a point objects in a three dimensional coordinate space. FIG. 3 illustrates the three dimensional coordinate space in which the pixels of the image of the biological specimen can be visualized. Axes of the three dimensional coordinate space correspond to the red component, green component, and blue component of the pixels. As a result, the pixels take a unique position in the coordinate space depending on values of the red components, the green components, and the blue components.

MC+1 Transformation Based on Translation and Rotation

In accordance with an exemplary embodiment of the present invention, image processing system 106 may apply a MC+1 transformation that involves reorienting the three-dimensional coordinate space of FIG. 3. The reorientation produces another three-dimensional coordinate space in which the pixels associated with the objects of interest are identifiable.

The reorientation consists of a translation and a rotation operation of the three dimensional coordinate space. For ease of visualization of the translation and rotation operation to be described herein, the positive object pixels, background pixels, and normal pixels, i.e., counter-stained object pixels, which define the image of the biological specimen are plotted in a two-dimensional coordinate space rather than the three dimensional coordinate space. Each pixel has red, green, and blue components, but the pixels are assumed, for purposes of illustration, to have just two components, the red components and the green components.

Figure 4:
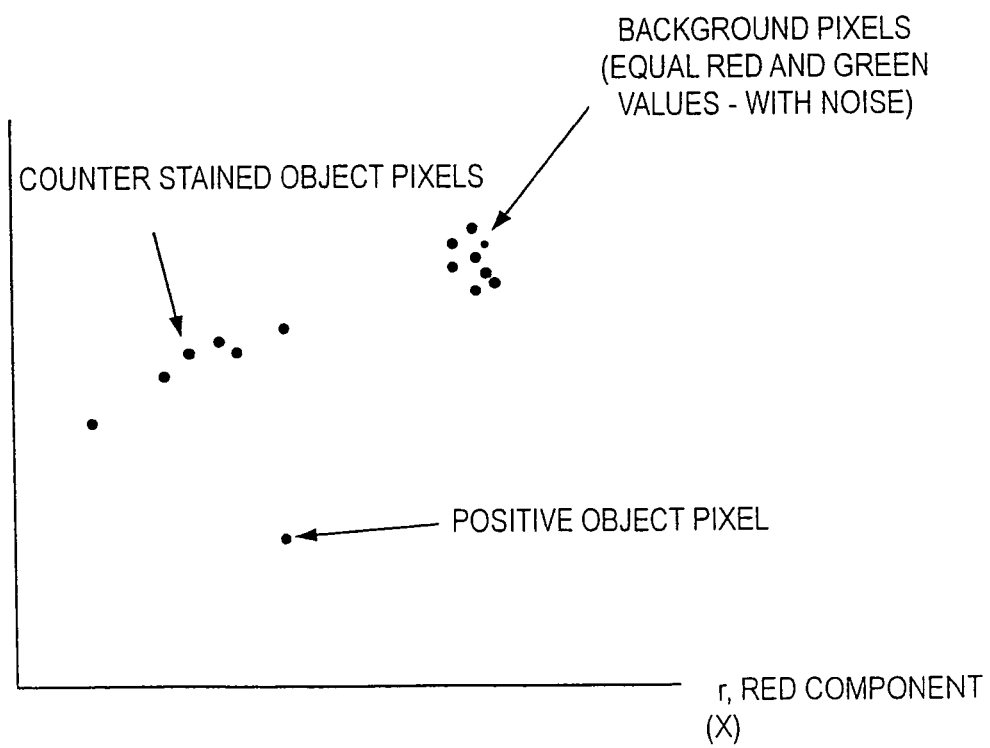
FIG. 4 illustrates a mapping of pixels of the exemplary image of the biological specimen into a two-dimensional coordinate space.

FIG. 4 illustrates plotting the pixels in a two dimensional coordinate space 150. In the two dimensional coordinate space, a red component of the pixel constitutes an "x-axis" and a green component of the pixel constitutes the "y axis." The two dimensional coordinate space has clusters of pixels. The clusters of pixels correspond to pixels defining the objects of interest, pixels defining the normal cells, and pixels defining the background areas of the image of the biological specimen.

The background pixels typically lie in a small cluster in the two dimensional coordinate space. The background pixels correspond to clear areas of the slide. As a result, the background pixels typically have a same value for both the red component and the green component. However, the background pixels will not have color components that are identical. Noise and illumination non-uniformities affect the color components of the background pixels. The noise and illumination non-uniformities cause the pixels to lie in the small cluster in the two dimensional coordinate space 150.

The cluster of the counter-stained object pixels lie in a roughly linear group extending from the background pixels. As the counterstained objects may represent normal cells, the counterstained object pixels are a different color from the background pixels. Noise and illumination non-uniformity, however, results in the counter stained object pixels being spread out in the two dimensional coordinate space 150. Additionally, varying degrees of staining intensity spreads the counter-stained object pixels. The variation in staining intensity makes the counter-stained object pixels lie in an elongated cluster extending from the background cluster.

Pixels defining the objects of interest will lie in another cluster of the two dimensional coordinate space. The pixels may lie in another cluster because the stain used to identify the positive object pixels will be different from the stain used to identify the counter-stained object pixels. The different stain results in the positive object pixels lying separately from the background pixels and the counter-stained object pixels in the two dimensional coordinate space 150.

Figure 5:
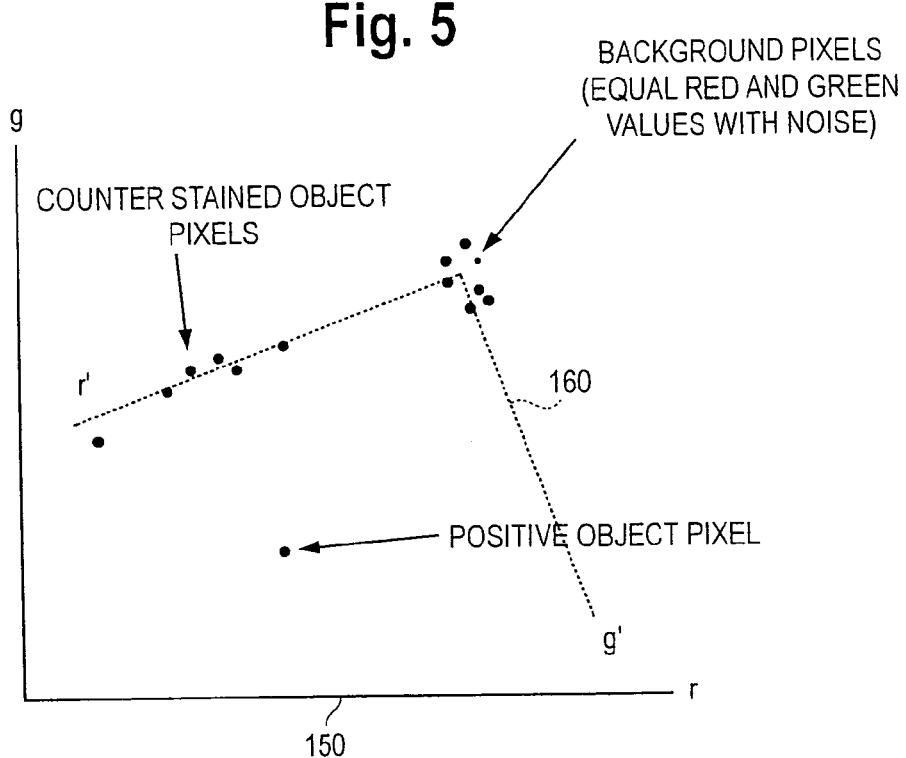
FIG. 5 illustrates rotating and translating the two-dimensional coordinate space of FIG. 4 to produce another two-dimensional coordinate space.

As illustrated by FIG. 5, the MC+1 transformation can be viewed as involving translating and rotating the two dimensional coordinate space 150 to produce another two dimensional coordinate space 160 having an origin at, for example, an average pixel value of the cluster of background pixels. The translation and rotation results in the counterstained pixels and the background pixels having nominally zero color components while the positive object pixels having non-zero color components. The two dimensional coordinates space 160, defined by axis r' and axis g', are not "actual" colors. Nonetheless, the non-zero color components of the positive object pixels make the positive object pixels readily identifiable in the two-dimensional coordinate space 160. The pixels, as plotted within the two-dimensional coordinate space 160, (or conceptually a three-dimensional coordinate space so oriented) define a transformed image. Additionally, the transformed image identifies the objects of interest, if any, in the biological specimen.

The transformation of the pixels according to the MC+1 transformation, conceptualized as a rotation and translation, involves mathematically complementing respective pixel components by a maximum pixel value (to translate the axes of the two dimensional coordinate space 150) and then applying rotation matrices (to rotate the axes of the two dimensional coordinate 150) to produce the two-dimensional coordinate space 160. The components of the pixels in the image of biological specimen may be quantized as 8 bit values ranging from 0 to 255, but other quantizations are also possible. If, however, the components are quantized as 8 bit values and a maximum component value is 255, then the processor of the image processing system 106 will execute computer instructions that result in a calculation of the complement of the respective pixel components as follows:

R'=255-R

G'=255-G

B'=255-B

Then, the processor of image processing system 106 executes computer instructions for performing three cascaded rotations to reduce the color components of the counter-stained pixels to zero and to maximize the color components of the positive object pixels:

The pixels in the first color space are rotated about the r' axis (defined by a translation of the r axis) and given by:

$$\begin{pmatrix} R'' \\ G'' \\ B'' \end{pmatrix} = \begin{pmatrix} ct & st & 0 \\ -st & ct & 0 \\ 0 & 0 & 1 \end{pmatrix} \begin{pmatrix} R' \\ G' \\ B' \end{pmatrix}$$

The matrix components are sins and cosines of the required rotation angle (theta). These are given by:

$$st := \frac{Gb}{(Rb^2 + Gb^2)^{0.5}} \quad ct := \frac{Rb}{(Rb^2 + Gb^2)^{0.5}}$$

where the subscript "b" denotes a component value for a respective component of the counterstained object pixel. The component value is based on a "typical" counterstained object pixel of the cluster of counter-stained object pixels, dependent on a particular staining method in use. The component value may be an average staining intensity, but other arrangements are also possible.

The pixels in the first color space are then rotated about the g' axis (defined by a translation of the g' axis) and given by:

$$\begin{pmatrix} R''' \\ G''' \\ B''' \end{pmatrix} = \begin{pmatrix} sp & 0 & cp \\ 0 & 1 & 0 \\ -cp & 0 & sp \end{pmatrix} \begin{pmatrix} R'' \\ G'' \\ B'' \end{pmatrix}$$

where the rotation coefficients are sins and cosines of an angle phi, given by $$sp := \frac{(Rb^2 + Gb^2)^{0.5}}{(Rb^2 + Gb^2 + Gb^2)^{0.5}} \quad cp := \frac{Bb}{(Rb^2 + Gb^2 + Bb^2)^{0.5}}$$

and the subscripts having the same meaning as before.

The pixels are then rotated about the b' axis (defined by a translation of the b' axis), thereby producing final color values in a rotated three dimensional coordinate space:

$$\begin{pmatrix} FinalR \\ FinalG \\ FinalB \end{pmatrix} = \begin{pmatrix} 1 & 0 & 0 \\ 0 & ca & -sa \\ 0 & sa & ca \end{pmatrix} \begin{pmatrix} R''' \\ G''' \\ B''' \end{pmatrix}$$

where the rotation coefficients are the sins and cosines of an angle alpha and are given by:

$$sa := \frac{[[-st \cdot (Rt) + ct \cdot Gt]]}{[[(-cp \cdot ct \cdot Rt) - cp \cdot st \cdot Gt + sp \cdot Bt]^2 + (-st \cdot Rt + ct \cdot Gt)^2]^{0.5}}$$

$$ca := \frac{(-cp \cdot ct \cdot Rt) - cp \cdot st \cdot Gt + sp \cdot Bt}{[[(-cp \cdot ct \cdot Rt) - cp \cdot st \cdot Gt + sp \cdot Bt]^2 + (-st \cdot Rt + ct \cdot Gt)^2]^{0.5}}$$

Here, the subscript "t" represents component values for a "typical" positive object pixel, also determined by the particular staining method in use.

The three rotation matrices, cascaded together, define an expression for the MC+1 value for each pixel in the image of the biological specimen. By calculating the MC+1 value for each pixel, the image processing system 106 transforms the image of the biological specimen to produce a transformed image. The transformed image consists of the MC+1 value for each of the pixels in the image of the biological specimen. Additionally, the transformed image identifies the objects of interest, if any, in the biological specimen. For example, the objects of interest may be defined by those pixels having an MC+1 value above a threshold value.

The expression for calculating the MC+1 value, i.e., the three rotation matrices, cascaded together, consists of a sum of a plurality of products between weighing coefficients and the complement of the red component, green component, or the blue component. The processor executes computer instructions stored in the memory for calculating the MC+1 transformation based on the sum of the plurality of products. Specifically, the expression is a sum of products between a first coefficient and the complement of the first component, e.g., red, for a pixel to be transformed, a second coefficient and the complement of the second component, e.g., green, for the pixel to be transformed, and a third coefficient and the complement of the third component, e.g., blue, for the pixel to be transformed, or:

MC+1 value=(-sa*cp*ct-ca*st)*R'+(-sa*cp*st+ ca*ct)*G'+(sa*sp)*B', where the first coefficient is -sa*cp*ct-ca*st, the second coefficient is -sa*cp*st+ca*ct, and the third coefficient is sa*sp, and R', G' and B' are the complements of the actual red, blue and green pixel values.

A variety of stains and counterstains can be used to make the objects of interest in the biological specimen more readily identifiable and the present invention is not limited to a particular staining chemistry. Values of the weighting coefficients in the above expression depend on a number of factors, including the actual staining chemistry used, the preparation of the stain and how it is used, and noise in the image and from other sources. AEC and Hematoxylin stains have been used which results for the first, second and third coefficients falling in a range of between approximately -0.7 to -0.8, 0.5 to 0.65, and 0.3 to 0.4, respectively. Actual values for the three components in one calculation were -0.721, 0.612, and 0.381, respectively. The weighting coefficients remain fixed throughout the transformation of the image of the biological specimen to the transformed image. Thus, in this particular example, the pixels in the image of the biological specimen, stained by AEC and Hematoxylin, are transformed by forming a following MC+1 value for each pixel in the image of the stained biological specimen:

MC+1 value=-0.721*(255-red)+0.612*(255-green)+ 0.381*(255-blue), where the red, green, and blue are components of the pixels in the image of the biological specimen. The transformed image is defined by the MC+1 value calculated for the pixels in the image of the biological specimen. Additionally, the objects of interest may be defined by those pixels having a MC+1 value above a threshold value.

Figure 6:
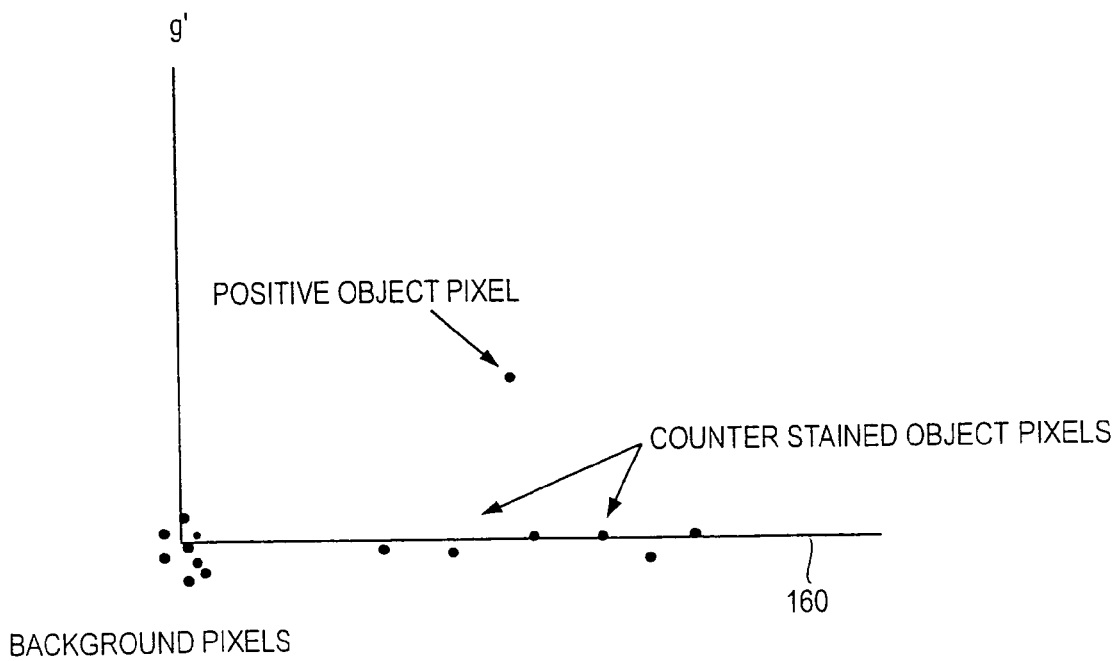
FIG. 6 illustrates a horizontal view of the other two-dimensional coordinate space of FIG. 5.

As shown by FIG. 6, the MC+1 transformation results in the color components of the background pixels and the counter-stained object pixels along the g' axis being nominally zero and the positive object pixels having a component along the g' axis. The pixels, as oriented in the two-dimensional coordinate space 160, define the transformed image in which the positive object pixels are visible in the transformed image and the background pixels and the counterstained object pixels are not visible.

Figure 7:
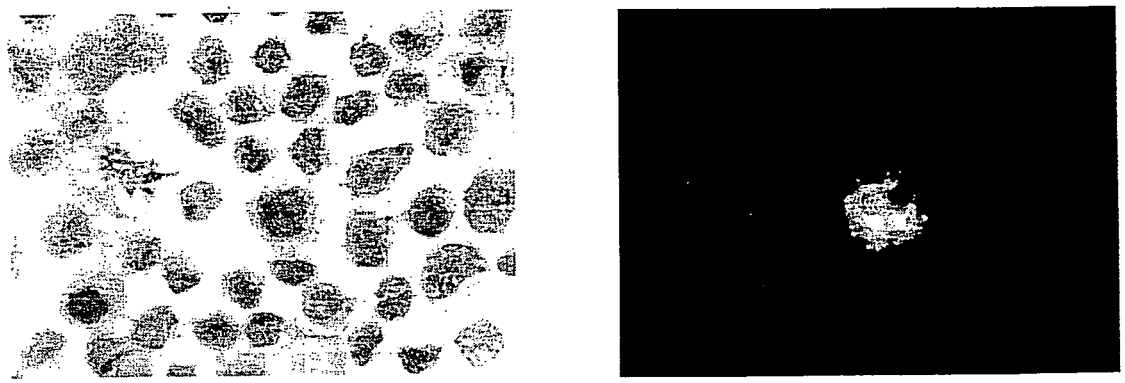
FIG. 7 illustrates results of a MC+1 transformation of the image of the biological specimen according to a rotation and translation operation.

FIG. 7 shows a transformed image produced as a result of applying the MC+1 transformation to the image of the biological specimen. Weighting the red component, green component, and blue component of the pixel values and forming a sum of weighted components, produces a new "color", or value. The new color or "value" for each of the pixels in the image of the biological specimen defines the transformed image. The transformed image is ideally suited for subsequent morphological processing, such as classification (thresholding), centroiding, dilation, or erosion so as to further refine identification of the objects of interest in the transformed image.

MC+1 Transformation Based on Vector Operations

In accordance with an alternative exemplary embodiment of the present invention, the image processing system 106 may apply an MC+1 transformation that involves vector operations, rather than a translation and rotation operation. The vector operations produce the transformed image which identifies the objects of interest, if any, in the biological specimen. The vector operations consist of defining two vectors in the three dimensional coordinate space. A counter-stained object vector extends from a typical background pixel of the background pixels through the counter-stained object pixels. On the other hand, a positive object vector extends from the typical background pixel to a positive object pixel. A difference between the positive object vector and the counter-stained object vector defines an MC+1 value for the positive object pixel. Steps of the MC+1 transformation based on the vector operations are different than steps of the MC+1 transformation based on the translation and rotation. However, as shown below, the results of the MC+1 transformation are the same.

Figure 8:
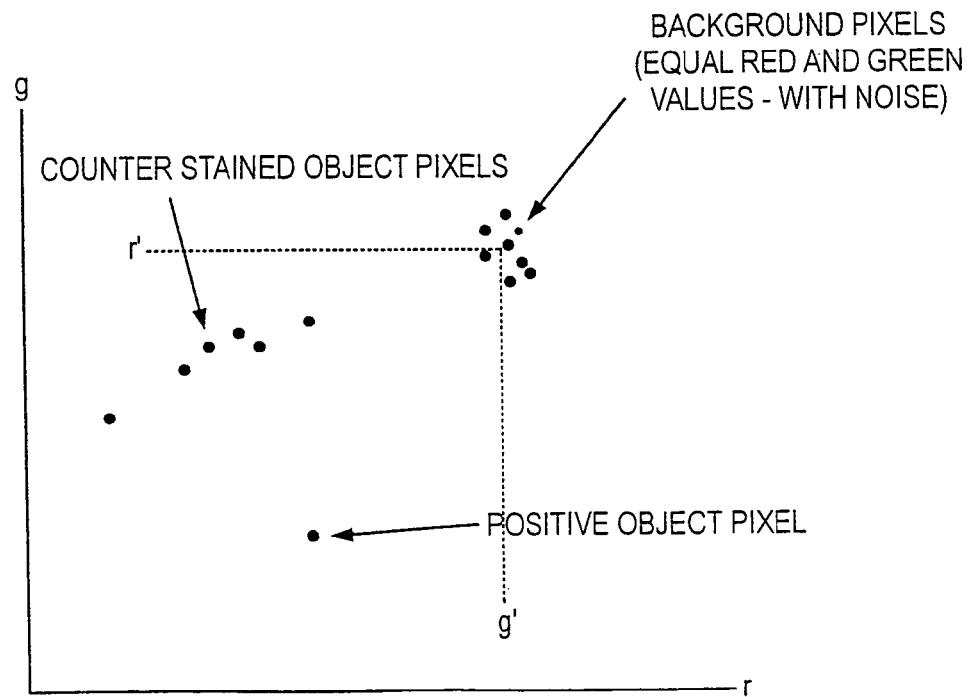
FIG. 8 illustrates defining yet another two-dimensional coordinate space which is a translation of the two-dimensional coordinate system of FIG. 3.

FIG. 8 illustrates transforming the pixels in the image of the biological specimen based on the vector operation. Again, for ease of visualization of the transformation operation to be described herein, the positive object pixels, the background pixels, and the counter-stained object pixels, which define the image of the biological specimen, are assumed to exist in an two dimensional coordinate space 190 rather than a three dimensional coordinate space. Each pixel has red, green, and blue components, but, for purposes of illustration, the pixels are assumed to have just two components, the red components and the green components.

The two dimensional coordinate space 190 has axes corresponding to the red component and green component of the pixels. Another two dimensional coordinate 194 includes axis r' and axis g', a translation of the axes defining the two dimensional coordinate space 190. The translation of the axes 190 result in an origin of the axes 194 being centered within cluster of the background pixels, e.g., at an average pixel value of the cluster of the background pixels.

Figure 9:
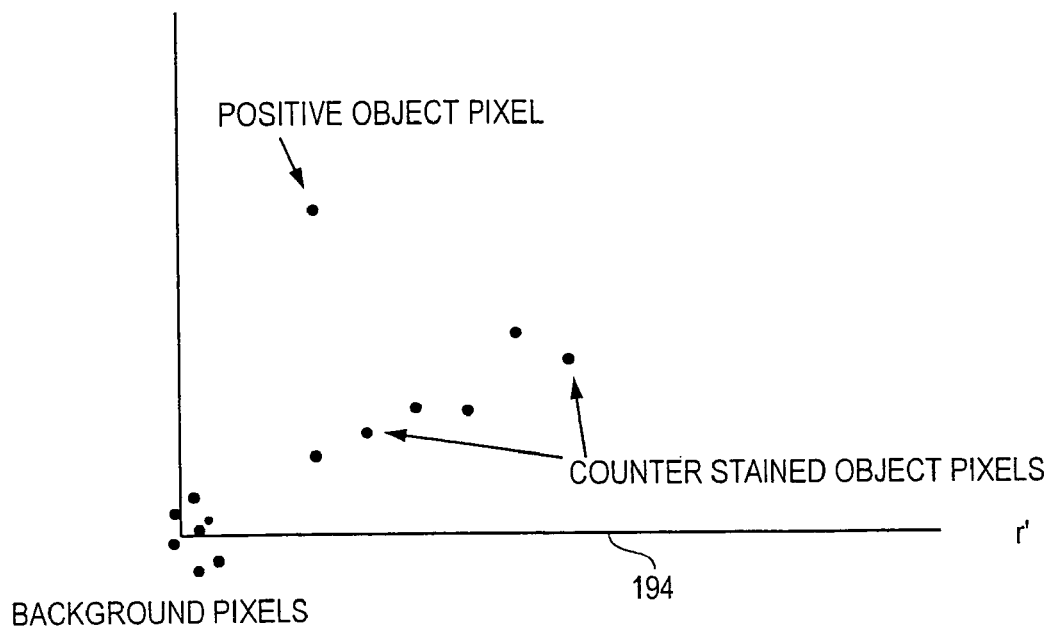
FIG. 9 illustrates a horizontal view of the two-dimensional coordinate space of FIG. 8.

FIG. 9 illustrates redrawing the two dimensional coordinate space 194 to facilitate an understanding of the transformation process, as described below.

Figure 10:
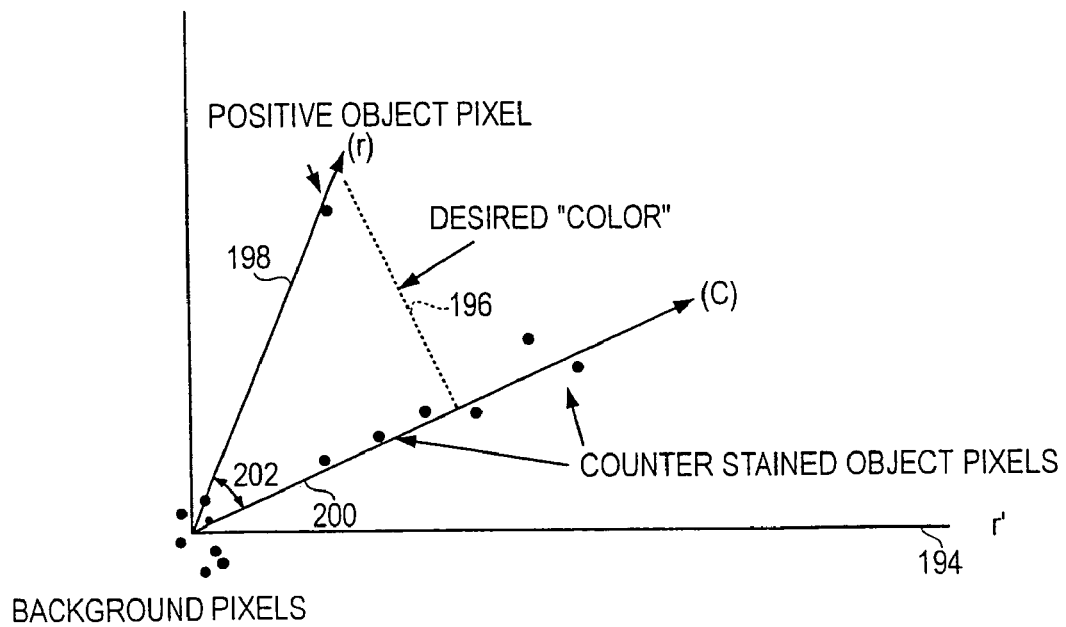
FIG. 10 illustrates defining vectors ranging from background pixels to positive object pixels and from background pixels to counterstained object pixels in the two dimensional coordinate space of FIG. 9.

FIG. 10 illustrates two vectors drawn from a cluster of the background pixels to the positive object pixel and counterstained object pixels, respectively, in the two dimensional coordinate space 194. A positive object pixel vector 198 extends from the cluster of the background pixels to the positive object pixel. Additionally, a counter-stained object pixel vector 200 extends through the counter-stained object pixels.

A dotted line 196 represents a difference between the positive object pixel vector 198 and the counter-stained object pixel vector 200 for the positive object pixel. The difference defines the MC+1 value for the positive object pixel.

Generally, the image of the biological image is transformed by calculating a difference between a vector and the counter-stained object pixel vector. The vector extends from the cluster of the background pixels to a pixel to be transformed, e.g., another background pixel, a positive object pixel, or a counterstained object pixel. The difference represents the MC+1 value for the pixel to be transformed. The difference for each pixel in the image of the biological specimen defines the transformed image. Additionally, the transformed image identifies the objects of interest, if any, in the biological specimen.

Elementary vector algebra mathematically defines the difference between the positive object pixel vector 198 and the counter-stained object pixel vector 200. The processor of the image processing system 106 calculates the difference by forming a complement of a first component, e.g., red component, a complement of a second component, e.g., green component, and a complement of a third component, e.g., blue component, for each of the pixels and then calculating a transform value, as described below.

The image processing system 106, in performing MC+1 transformation based on the vector operations, has computer instructions stored in the memory and executable by the processor for calculating a dot product of two vectors. The dot product is:

$$P \text{ dot } C = \text{Mag}(P) * \text{Mag } C * \cos(\text{included angle}),$$

where the included angle represents the angle between the positive object vector and the counter stained object vector, P represents a magnitude of the positive object pixel vector, P, and C represents the magnitude of the counter-stained object vectors, C.

Expanding the dot product, the MC+1 value, or transform based on the vector operation is represented as:

$$MC+1 \text{ value} = \text{sqrt}((R'^2 + G'^2 + B'^2) * (Rb^2 + Gb^2 + Bb^2) - (R'*Rb + G'*Gb + B'*Bb)^2)$$

where R', G', and B' represent a complimented red component, green component, and blue component, of the pixels in the image of the biological specimen. Additionally, the quantities Rb, Gb, and Bb are the complemented component values of pixels for a "typical" counterstained object. The image processing system 106 transforms the image of the biological specimen by calculating the MC+1 value for each pixel the image of the biological specimen. The MC+1 value for each of the pixels defines a transformed image which identifies the objects of interest, if any, in the biological specimen. For example, the objects of interest may be defined by those pixels having a MC+1 value above a threshold value. Additionally, morphological processing can be applied to the transformed image so as to further refine identification of the objects of interest.

Figure 11:
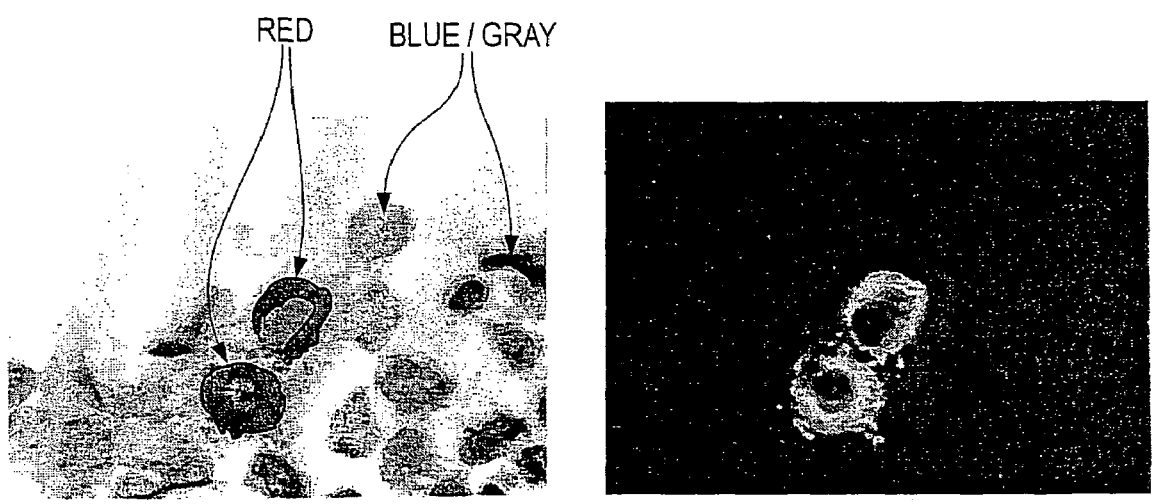
FIG. 11 illustrates results of the MC+1 transformation of the image of the biological specimen according to vector operations.

FIG. 11 illustrates the transformed image produced as a result of applying the MC+1 transform based on the vector operation to an image of the biological specimen. Comparing FIG. 7 to FIG. 11, the MC+1 transformation based on the vector operation produces same results as the MC+1 transformation based on the translation and rotation operation. Thus, the MC+1 transformation based on the vector operation is another method for identifying object of interest in the image of the biological specimen.

Quantitative Chromatic Transformation (QCT)

Instead of, or in addition to the MC+1 transformation, the image processing system 106 may apply a QCT to identify the objects of interest in the image of the biological specimen. The QCT results in a characterization of a quantitative amount of absorbing molecules sampled by a pixel.

The QCT involves calculating three new quantities from the red component, the green component, and the blue component of the pixels in the image of the biological specimen. The three new quantities, X, Y, and Z linearly relate, to a sampled pixel, a quantitative amount of absorbing molecules, N. Each of the three new quantities X, Y, and Z involves calculating a quotient. The quotient consists of first value divided by a second value, where the first value is a square of a component, e.g., red, green, blue, of a pixel to be transformed and the second value is product of two different components, e.g., red, green, blue, of the pixel to be transformed.

The following expressions define the quotient, or, a number of absorbing molecules sampled by a pixel having a red component, r, a green component, g, and a blue component, b, respectively:

$$X = \log(r^2/(g \times b)) \quad Y = \log(g^2/(r \times b)) \quad Z = \log(b^2/(r \times g))$$

One or more of these three quantities represents an acceptable estimate of N. As a result, the processor of the image processing system 106 may execute computer instructions for calculating the amount of absorbing molecules per pixel, as described by the above expressions. Preferably, however, the average of these quantities produces a better estimate of N. The processor may execute computer instructions for applying weighting coefficients, $k_x$, $k_y$, and $k_z$ to weight the three component values X, Y, and Z such that the component with the most noise contributes the least to the weighted average and vice-versa. The weighing coefficients, as applied to the three component values, produce a weighted average, i.e., a QCT value:

$$\text{QCT value} = k_x X + k_y Y + k_z Z$$

Optimal estimation theory defines the weighing coefficients. Taking three estimates for a quantity X (not the same quantity as the X of QCT, but instead a variant X: X1, X2, and X3), the three estimates can be averaged to reduce the noise of the final estimate, or:

$$X := \frac{X1 + X2 + X3}{3} \qquad (1)$$

or $$X := \frac{1}{3} \cdot X1 + \frac{1}{3} \cdot X2 + \frac{1}{3} \cdot X3$$

For such a case, the noise (standard deviation) of the final estimate of X is given in terms of the standard deviations of each estimate as:

$$(\sigma)^2 := \left(\frac{1}{3} \cdot \sigma_1\right)^2 + \left(\frac{1}{3} \cdot \sigma_2\right)^2 + \left(\frac{1}{3} \cdot \sigma_3\right)^2$$

If all the standard deviations are equal, then the noise equals a root sum squared (RSS) of X1, X2, and X3. Thus, the processor may execute computer instructions stored in the memory for weighing the amount of absorbing molecules given by X, Y, and Z, by coefficients $k_x$, $k_y$, and $k_z$ equal to ⅓, to produce the weighted average, i.e., the QCT value. The QCT value for each of the pixels in the image of the biological specimen defines a transformed image. The transformed image identifies the object of interest in the biological specimen, if any. For example, the objects of interest may be defined by those pixels having a QCT value above a threshold value.

Alternatively, the processor of the image processing system 106 may execute computer instructions that produce a weighted average. The weighted average is calculated as a result of applying a small weight to the estimate of the amount of absorbing molecules with highest noise and a large weight to the estimate of the amount of absorbing molecules value with lowest noise. So, instead of forming an average with equal weighting coefficients, a weighted average can be produced according to:

$$X := k1 \cdot X1 + k2 \cdot X2 + k3 \cdot X3$$

where the "k's" are not equal, and are subject to:

$$k1 + k2 + k3 := 1$$

The noise values will combine according to:

$$(\sigma)^2 := (k1 \cdot \sigma_1)^2 + (k2 \cdot \sigma_2)^2 + (k3 \cdot \sigma_3)^2$$

$$\sigma^2 := k1^2 \cdot \sigma 1^2 + k2^2 \cdot \sigma 2^2 + k3^2 \cdot \sigma 3^2$$

The values for k1, k2, and k3 can be obtained by solving:

$$\frac{d}{dk1}\sigma^2 := 0 \qquad \frac{d}{dk2}\sigma^2 := 0 \qquad \frac{d}{dk3}\sigma^2 := 0$$

These solutions provide the following answers for the weighting coefficients.

$$k1 := \frac{\sigma 2^2 \cdot \sigma 3^2}{\sigma 1^2 \cdot \sigma 2^2 + \sigma 1^2 \cdot \sigma 3^2 + \sigma 2^2 \cdot \sigma 3^2} \qquad (2)$$

-continued $$k2 := \frac{\sigma 2^2 \cdot \sigma 3^2}{\sigma 1^2 \cdot \sigma 2^2 + \sigma 1^2 \cdot \sigma 3^2 + \sigma 2^2 \cdot \sigma 3^2}$$

$$k3 := \frac{\sigma 1^2 \cdot \sigma 2^2}{\sigma 1^2 \cdot \sigma 2^2 + \sigma 1^2 \cdot \sigma 3^2 + \sigma 2^2 \cdot \sigma 3^2}$$

Thus, the QCT value may be calculated as a result of calculating variances for X, Y, and Z, calculating the weighting coefficients, and then weighting the three estimates of absorbing molecules by the weighting coefficients to obtain the weighed average.

Taking, for instance, the definition of X (without the logarithm):

$$X \equiv \frac{r^2}{gxb}$$

where r, g, and b are the pixel values for the red, green, and blue component, respectively, for a pixel in the image of the biological specimen. For each of the component values of the pixels, Beer's Law shows that:

$$r = r_o 10^{-k_r * C * l} \quad g = g_0 10^{-k_g * C * l} \text{ and } b = b_0 10^{-k_b * C * l}$$

That is, the component values of the pixels is exponentially related to an absorption constant for each spectral band, an analyte concentration C, i.e., the number of absorbing molecules, and a path length through the sample. Substitution into the definition of X above results in:

$$X = \frac{r_0^2 10^{-2k_r Cl}}{g_0 b_0 10^{-k_g Cl} 10^{-k_b Cl}}$$

For a colorimetrically calibrated system, $$\frac{r_0^2}{g_0 b_0} = 1,$$

the above expression can be simplified to obtain:

$$X = \frac{10^{-2k_r Cl}}{10^{-k_g Cl} 10^{-k_b Cl}} = 10^{-Cl(2k_r + k_g + k_b)}$$

Taking the log of this expression, and solving for the C*l product (which is the product of the analyte concentration times the path length) produces the following quantity:

$$C * l \equiv N = -\frac{\log(X)}{2k_r + k_g + k_b}$$

The number of absorbing molecules sampled by a pixel may also be estimated for the other two quantities of QCT, namely the Y and Z quantities. The three different estimates of N become:

$$N_X = -\frac{\log(X)}{2k_r + k_g + k_b}$$

$$N_Y = -\frac{\log(Y)}{k_r + k_g + k_b}$$

$$N_Z = -\frac{\log(Z)}{k_r + k_g + k_b}$$

Given variances for the red components, green components, and blue components of the pixels, the variances of these three quantities are calculated as:

$$\sigma_{N_X}^2 = \frac{1}{3(2k_r + k_g + k_b)}\left[\left(\frac{d\log X}{dr}\right)^2 \sigma_r^2 + \left(\frac{d\log X}{dg}\right)^2 \sigma_g^2 + \left(\frac{d\log X}{db}\right)^2 \sigma_b^2\right] \quad \text{eq (3)}$$

From the definition of X:

$$X \equiv \frac{r^2}{gb} \text{ and } \log X = \frac{1}{2.303}\ln X$$

$$\frac{d\log X}{dr} = \frac{1}{2.303}\frac{d\ln X}{dr} = \frac{1}{2.303}\frac{1}{X}\left(\frac{2r}{gb}\right) = \frac{1}{2.303}\frac{gb}{r^2}\left(2\frac{r}{gb}\right) = \frac{1}{2.303}\frac{2}{r}$$

And similarly for the other derivatives:

$$\frac{d\log X}{dg} = -\frac{1}{2.303}\frac{1}{g}, \text{ and}$$

$$\frac{d\log X}{db} = -\frac{1}{2.303}\frac{1}{b}$$

Substitution of these expression into eq (3) yields:

$$\sigma_{N_X}^2 = \frac{1}{3*2.303^2*(2k_r + k_g + k_b)}\left[\left(\frac{2}{r}\right)^2 \sigma_r^2 + \left(\frac{1}{g}\right)^2 \sigma_g^2 + \left(\frac{2}{b}\right)^2 \sigma_b^2\right]$$

For equal variances for the red components, green components, and the blue components:

$$\sigma_{N_X}^2 = \frac{1}{3*2.303^2*(2k_r + k_g + k_b)}\left[\left(\frac{2}{r}\right)^2 + \left(\frac{1}{g}\right)^2 + \left(\frac{1}{b}\right)^2\right]\sigma^2$$

This same analysis can be applied to calculate the variances for Y and Z. The final three expressions are:

$$\sigma_{N_X}^2 = \frac{1}{3*2.303^2*(2k_r + k_g + k_b)}\left[\left(\frac{2}{r}\right)^2 + \left(\frac{1}{g}\right)^2 + \left(\frac{1}{b}\right)^2\right]\sigma^2 \quad \text{eqs 4}$$

$$\sigma_{N_Y}^2 = \frac{1}{3*2.303^2*(k_r + 2k_g + k_b)}\left[\left(\frac{1}{r}\right)^2 + \left(\frac{2}{g}\right)^2 + \left(\frac{1}{b}\right)^2\right]\sigma^2$$

$$\sigma_{N_Z}^2 = \frac{1}{3*2.303^2*(k_r + k_g + 2k_b)}\left[\left(\frac{1}{r}\right)^2 + \left(\frac{1}{g}\right)^2\left(\frac{2}{b}\right)^2\right]\sigma^2$$

Finally, making use of eq (2) and using the values from eq (4) and substituting:

$$C_X = \frac{1}{2k_r + k_g + k}$$

$$C_Y = \frac{1}{k_r + 2k_g + k}$$

$$C_Z = \frac{1}{k_r + k_g + 2k}$$

$$k_X = \frac{\sigma_{N_Y}^2 \sigma_{N_Z}^2}{\sigma_{N_X}^2 \sigma_{N_Y}^2 + \sigma_{N_X}^2 \sigma_{N_Z}^2 + \sigma_{N_Y}^2 \sigma_{N_Z}^2}$$

result in:

$$k_x = \frac{\frac{1}{C_Y C_Z}\left[\left(\frac{1}{r}\right)^2 + \left(\frac{2}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right]}{\frac{1}{C_X}\frac{1}{C_Y}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{2}{g}\right)^2 + \left(\frac{1}{b}\right)^2\right] + \frac{1}{C_X}\frac{1}{C_Z}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right] + \frac{1}{C_Y}\frac{1}{C_Z}\left[\left(\frac{1}{r}\right)^2 + \left(\frac{2}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right]}$$

$$k_y = \frac{\frac{1}{C_X C_Z}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right]}{\frac{1}{C_X}\frac{1}{C_Y}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{2}{g}\right)^2 + \left(\frac{1}{b}\right)^2\right] + \frac{1}{C_X}\frac{1}{C_Z}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right] + \frac{1}{C_Y}\frac{1}{C_Z}\left[\left(\frac{1}{r}\right)^2 + \left(\frac{2}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right]}$$

$$k_z = \frac{\frac{1}{C_X C_Y}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{2}{g}\right)^2 + \left(\frac{1}{b}\right)^2\right]}{\frac{1}{C_X}\frac{1}{C_Y}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{2}{g}\right)^2 + \left(\frac{1}{b}\right)^2\right] + \frac{1}{C_X}\frac{1}{C_Z}\left[\left(\frac{2}{r}\right)^2 + \left(\frac{1}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right] + \frac{1}{C_Y}\frac{1}{C_Z}\left[\left(\frac{1}{r}\right)^2 + \left(\frac{2}{g}\right)^2 + \left(\frac{1}{b}\right)^2\right]\left[\left(\frac{1}{r}\right)^2 + \left(\frac{1}{g}\right)^2 + \left(\frac{2}{b}\right)^2\right]}$$

Thus, $k_x$, $k_y$, and $k_z$, as above, defines the weighting coefficients for X, Y, and Z according to the QCT. The processor of the image processing system 106 may apply these weighting coefficients, instead of equal weighting coefficients of ⅓, to calculate the QCT value for each of the pixels. The QCT value for each of the pixels defines a transformed image which identifies the objects of interest in the biological specimen, if any. For example, the objects of interest may be defined by those pixels having a QCT value above a threshold value. Additionally, morphological processing can be applied to the transformed image so as to further refine identification of the objects of interest.

Exemplary embodiments of the present invention have thus been illustrated and described. It will be understood, however, that changes and modifications may be made to the invention as described without deviating from the spirit and scope of the invention, as defined by the following claims.

For example, a general-purpose computer associated with the microscope, in a separate workstation, a programmable microprocessor, or any other suitable computing device, may execute the instructions that code the color space transformations. The details of the microscope system, the cameras used to capture the images of the slide are likewise are not particularly pertinent and can vary widely.

What is claimed is:

1. A method for identifying objects of interest in a biological specimen, the objects of interest being identified from normal cells and background areas of the biological specimen, the method comprising:

obtaining an image of the biological specimen, the image of the biological specimen comprising positive object pixels, counterstained object pixels, and background pixels;

storing pixel values representing the image in a memory;

executing instructions in a computing device that operate on said stored pixel values so as to transform the image of the biological specimen to produce a transformed image, the transformed image being characterized by a three dimensional coordinate space, the image of the biological specimen being transformed by said instructions by orienting a cluster of the background pixels at an origin of the three-dimensional coordinate space and the counter-stained object pixels substantially along an axis of the three-dimensional coordinate space whereby the positive object pixels lie substantially between axes of the three-dimensional coordinate space, whereby the transformed image assists in identification of the objects of interest, if any, in the biological specimen.

2. The method of claim 1, wherein the origin of the three-dimensional coordinate space is located at an average of the cluster of background pixels.

3. The method of claim 1, wherein orienting the cluster of the background pixels and the counter-stained object pixels comprises translating and rotating the axes of the three-dimensional coordinate space.

4. The method of claim 1, further comprising morphologically processing the transformed image to refine identification of the objects of interest, if any, in the biological specimen.

5. A method for identifying objects of interest in a biological specimen, the objects of interest being identified from normal cells and background areas of the biological specimen, the method comprising:

obtaining an image of the biological specimen, the image of the biological specimen comprising positive object pixels, counter-stained object pixels, and background pixels, the positive object pixels, the counter-stained object pixels, and the background pixels each being defined by a first component, a second component, and a third component of a three-dimensional coordinate space;

storing pixel values representing the first, second and third components in a memory;

executing instructions in a computing device that operate on said stored pixel values so as to define (a) a counter-stained object vector in the three dimensional coordinate space, the counter-stained object vector extending from a cluster of the background pixels through the counter-stained object pixels whereby the counter-stained object pixels lies substantially along the counter-stained object vector; and (b) positive object vectors extending from the cluster of the background pixels to the positive object pixels;

said instructions transforming the image of the biological specimen to produce a transformed image, the image of the biological specimen being transformed by calculating differences between the positive object vectors and the counter-stained object vector, whereby the transformed image assists in identifying the objects of interest, if any, in the biological specimen.

6. The method of claim 5, wherein the counter-stained object vector extending from a cluster of the background pixels through the counter-stained object pixels comprises the counter-stained object vector extending from an average of the cluster of background pixels through the counter-stained object pixels.

7. The method of claim 5, further comprising morphologically processing the transformed image to refine identification of the objects of interest, if any, in the biological specimen.

8. A system for identifying objects of interest in a biological specimen, the objects of interest being identified from normal cells and background areas of the biological specimen, the system comprising:

a processor;

memory;

computer instructions stored in memory and executable by the processor for performing the functions of:

obtaining an image of the biological specimen, the image of the biological specimen comprising positive object pixels, counterstained object pixels, and background pixels;

transforming the image of the biological specimen to produce a transformed image, the transformed image being characterized by a three-dimensional coordinate space, the image of the biological specimen being transformed by orienting a cluster of the background pixels at an origin of the three-dimensional coordinate space and the counter-stained object pixels substantially along an axis of the three-dimensional coordinate space whereby the positive object pixels lie substantially between axes of the three-dimensional coordinate space, whereby the transformed image assists in identifying objects of interest, if any, in the biological specimen.

9. The system of claim 8, wherein the first, the second, and the third components of the pixel to be transformed are red, green, and blue components, respectively.

10. The system of claim 8, further comprising computer instructions executable by the processor for performing the function of morphologically processing the transformed image to refine identification of the objects of interest, if any, in the biological specimen.

11. A system for identifying objects of interest in a biological specimen, the objects of interest being identified from normal cells and background areas of the biological specimen, the system comprising:

a processor;

memory;

computer instructions stored in memory and executable by the processor for performing the functions of:

obtaining an image of the biological specimen, the image of the biological specimen comprising positive object pixels, counterstained object pixels, and background pixels, the positive object pixels, the counter-stained object pixels, and the background pixels each being defined by a first component, a second component, and a third component of a three-dimensional coordinate space;

defining (a) a counter-stained object vector in the three dimensional coordinate space, the counter-stained object vector extending from a cluster of the background pixels through the counter-stained object pixels whereby the counter-stained object pixels lies substantially along the counter-stained object vector; and (b) positive object vectors extending from the cluster of the background pixels to the positive object pixels;

transforming the image of the biological specimen to produce a transformed image, the image of the biological specimen being transformed by calculating differences between the positive object vectors and the counter-stained object vector, whereby the transformed image identifies the objects of interest, if any, in the biological specimen.

12. The system of claim 11, further comprising computer instructions executable by the processor for performing the function of morphologically processing the transformed image to refine identification of the objects of interest, if any, in the biological specimen.

\* \* \* \* \*